(12) United States Patent
Heck et al.

(10) Patent No.: US 9,610,127 B2
(45) Date of Patent: Apr. 4, 2017

(54) PROTECTIVE CONTAINER FOR HOLDING REUSABLE DIAGNOSTIC COMPONENTS

(71) Applicant: Roche Diagnostics Operations, Inc., Indianapolis, IN (US)

(72) Inventors: Wolfgang Heck, Frankenthal (DE); Bernd Roesicke, Mannheim (DE); Gerhard Frisch, Edingen-Neckarhausen (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 256 days.

(21) Appl. No.: 14/319,445

(22) Filed: Jun. 30, 2014

(65) Prior Publication Data

US 2014/0316223 A1    Oct. 23, 2014

Related U.S. Application Data

(63) Continuation of application No. 12/971,957, filed on Dec. 17, 2010, now Pat. No. 8,783,102.

(30) Foreign Application Priority Data

Dec. 18, 2009 (EP) .................................. 09179802

(51) Int. Cl.
*A61B 19/02* (2006.01)
*A61B 5/145* (2006.01)
(Continued)

(52) U.S. Cl.
CPC .......... *A61B 19/026* (2013.01); *A61B 5/1495* (2013.01); *A61B 5/14532* (2013.01);
(Continued)

(58) Field of Classification Search
CPC ............ A61B 5/14532; A61B 5/14865; A61B 5/1486; A61B 5/1473; A61B 5/1468;
(Continued)

(56) References Cited

U.S. PATENT DOCUMENTS 4,801,271 A    1/1989   Piper
5,215,474 A *  6/1993   Rotella ............. H01R 13/6485
                                              361/220
(Continued)

FOREIGN PATENT DOCUMENTS

EP    1 418 438 A2    5/2004
EP      1669020 A1    6/2006
(Continued)

OTHER PUBLICATIONS

EPO machine translation of specification and claims of EP 1972267 A1, machine translation done Jan. 12, 2014.
(Continued)

*Primary Examiner* — Daniel S Larkin
*Assistant Examiner* — Nathaniel Kolb
(74) *Attorney, Agent, or Firm* — Bose McKinney & Evans LLP

(57) ABSTRACT

A protective container for holding a reusable control part of a transcutaneous sensor system for detecting at least one analyte in a bodily fluid is disclosed. The control part includes at least one coupling, which has at least one sensor coupling for connection to at least one transcutaneous sensor. The protective container has at least one container housing. The control part can be held in the container housing. The container housing is adapted to shield the control part from environmental influences. The container housing also has at least one connector which can be connected to the coupling and seals the latter in a media-tight fashion.

9 Claims, 6 Drawing Sheets

(51) Int. Cl.
    *A61B 5/1486* (2006.01)
    *A61B 5/00* (2006.01)
    *A61B 5/1495* (2006.01)
    *A61B 50/30* (2016.01)
    *A61B 46/10* (2016.01)

(52) U.S. Cl.
    CPC ...... *A61B 5/14546* (2013.01); *A61B 5/14865* (2013.01); *A61B 5/6849* (2013.01); *A61B 46/10* (2016.02); *A61B 50/30* (2016.02); *A61B 2560/0431* (2013.01); *A61B 2562/18* (2013.01); *A61B 2562/182* (2013.01)

(58) Field of Classification Search
    CPC .............. A61B 5/14503; A61B 5/6847; A61B 2562/18; A61B 2562/225; A61B 2562/227; A61B 2562/182
    USPC .................................. 600/309, 347, 365, 366
    See application file for complete search history.

(56) References Cited

U.S. PATENT DOCUMENTS

| | | | |
|---|---|---|---|
| 5,543,727 | A | 8/1996 | Bushard et al. |
| 5,980,498 | A | 11/1999 | Brown et al. |
| 6,360,888 | B1 | 3/2002 | McIvor et al. |
| 6,594,156 | B1 | 7/2003 | Van Antwerp et al. |
| 6,632,855 | B1 * | 10/2003 | Beverly ............... A01N 25/10 428/521 |
| 6,740,059 | B2 * | 5/2004 | Flaherty ............ A61M 5/14248 600/151 |
| 7,108,395 | B2 | 9/2006 | Correa |
| 7,494,465 | B2 | 2/2009 | Brister et al. |
| 7,519,408 | B2 | 4/2009 | Rasdal et al. |
| 2001/0034479 | A1 | 10/2001 | Ring et al. |
| 2003/0017728 | A1 | 1/2003 | Ogawa |
| 2004/0122353 | A1 | 6/2004 | Shahmirian et al. |
| 2005/0174727 | A1 | 8/2005 | Thomas et al. |
| 2005/0215871 | A1 | 9/2005 | Feldman et al. |
| 2006/0183984 | A1 | 8/2006 | Dobbles et al. |
| 2007/0208246 | A1 * | 9/2007 | Brauker ........... A61B 5/150022 600/365 |
| 2008/0161656 | A1 * | 7/2008 | Bruce .................. A61B 5/0031 600/300 |
| 2008/0234561 | A1 | 9/2008 | Roesicke et al. |
| 2008/0242962 | A1 * | 10/2008 | Roesicke ........... A61B 5/14532 600/347 |
| 2009/0300616 | A1 | 12/2009 | Sicurello et al. |
| 2010/0230285 | A1 * | 9/2010 | Hoss .................. A61B 5/14532 204/415 |
| 2011/0213225 | A1 | 9/2011 | Bernstein et al. |
| 2011/0319729 | A1 | 12/2011 | Donnay et al. |
| 2012/0010642 | A1 | 1/2012 | Lee et al. |
| 2012/0028504 | A1 * | 2/2012 | Coggins ............. A61B 5/04286 439/628 |
| 2012/0130212 | A1 | 5/2012 | Pluta et al. |

FOREIGN PATENT DOCUMENTS

| | | |
|---|---|---|
| EP | 1 972 267 A1 | 9/2008 |
| EP | 1 972 275 A1 | 9/2008 |
| JP | 2010279498 A | 12/2010 |
| WO | WO 9956613 A1 | 11/1999 |
| WO | WO 2006/133305 A2 | 12/2006 |

OTHER PUBLICATIONS

Derwent abstract of EP 1972267 A1, Derwent Acc No. 2008-M53220, Derwent Week: 201310, Copyright 2014 Thomson Reuters.

* cited by examiner

PROTECTIVE CONTAINER FOR HOLDING REUSABLE DIAGNOSTIC COMPONENTS

RELATED APPLICATIONS

This is a continuation of application Ser. No. 12/971,957 filed Dec. 17, 2010, which claims priority to EP 09 179 802.5 filed Dec. 18, 2009, both of which are hereby incorporated by reference in their entirety.

FIELD OF THE INVENTION

The invention relates to a protective container for holding a reusable control part of a transcutaneous sensor system. In some embodiments, the invention relates to a kit, comprising a protective container and a reusable control part, and a sensor device for detecting at least one analyte in a bodily fluid. Still other embodiments relate to a method for protecting a reusable control part of a transcutaneous sensor system for detecting at least one analyte. Such devices and methods are used in particular in the field of medical diagnostics, for example in hospitals, care facilities, or private surroundings in order to detect, qualitatively or quantitatively, one or more analytes, such as, for example, glucose, lactate, cholesterol, triglycerides or other types of analytes, in one or more bodily fluids, such as, for example, interstitial fluid or blood.

Monitoring certain bodily functions, more particularly monitoring one or more concentrations of certain analytes, plays an important role in the prevention and treatment of various diseases. Without restricting the scope of the invention and further possible applications, several embodiments of the invention will be described in the following text with reference to blood-glucose monitoring. However, other embodiments of the invention can be applied to other types of analytes and/or monitoring other types of bodily functions. For example, monitoring another type of bodily function is encompassed by the phrase "detecting at least one analyte in a bodily fluid" as an alternative to a qualitative and/or quantitative detection of an analyte in a bodily fluid, or in addition thereto.

BACKGROUND

In addition to so-called spot measurements, in which a sample of a bodily fluid is taken from a user in a targeted fashion and examined with respect to the analyte concentration, continuous measurements are becoming increasingly common. Thus, in the recent past, continuous measuring of glucose in the interstitial space (also referred to as continuous monitoring, CM), for example, has been established as another important method for managing, monitoring and controlling a diabetes state. Continuous monitoring is often restricted to type I diabetics, that is to say diabetics who usually also carry an insulin pump. Continuous monitoring generally employs the use of directly implanted electrochemical sensors, which are often referred to as needle-type sensors (NTS). In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 and in US Pub. No. 2008/0242962 A1 both of which are incorporated herein by reference.

Hence, current continuous monitoring systems are generally transcutaneous systems. This means that the actual sensor is arranged under the skin of the user. However, an evaluation and control part of the system (also referred to as a patch) is generally situated outside of the body of the user, that is to say outside of the human or animal body. In the process, the sensor is generally applied using an insertion instrument such as that exemplified in U.S. Pat. No. 6,360,888 B1 which is incorporated herein by reference. Other types of insertion instruments are also known. A sensor is generally worn for approximately one week. After that, influences such as enzymes being used up and/or a sealing off in the body generally reduce the sensitivity of the sensor, or it is expected that the sensor fails. Increasing the duration of wear is an area of current research. However, this means that the sensor and, optionally, components directly connected to the former such as an insertion needle, should be designed as replaceable components. Accordingly, the sensor and optionally further replaceable components generally constitute a so-called disposable. By contrast, the evaluation and control part of the system is reused in most cases. Accordingly, this evaluation and control part is generally referred to as a so-called reusable.

Subdividing the transcutaneous sensor system like this into at least one disposable and at least one reusable in principle leads to the problem of requiring a detachable interface between the evaluation and control part (patch) and the sensor. This interface is generally subjected to being touched by the user to a greater or lesser extent, depending on the design of the system. This interface is subject to sterilization and disinfection insofar as the implantable sensor needs to be sterilized after production for reasons of biocompatibility and hygiene, and insofar as the reusable generally needs to be disinfected after use.

In principle, there are various means for sterilizing the sensor. However, since currently known sensors typically include sensor chemicals and have fluidic contact with the bodily fluid, for example the interstitial fluid, both chemical and thermal sterilization can generally be excluded. Traces of chemical sterilization, for example traces of ethylene oxide, could remain in the sensor chemicals, which, in the implanted state, could subsequently lead to ingress of the sterilization means into the body tissue. By contrast, thermal sterilization could destroy sensitive sensor chemicals, e.g. enzymes. Thus, in general, only radiation sterilization, for example using beta radiation, remains available as a method for sterilizing the sensor. However, radiation doses at the required strength often damage electronic components. Partial shielding of these components, as described in EP 1 178 841 B1, which is incorporated herein by reference, for example, requires great complexity in the production process.

Many currently pursued approaches for continuously monitoring analyte concentrations provide for a so-called bodymount to be stuck onto the skin of a user by means of a plaster. An example of such a system is described in US Pub. No. 2008/024962 A1 and EP 1 972 275 A1 both of which are incorporated herein by reference. The bodymount is likewise designed as a disposable. It contains a battery, an electronic storage medium (for example an EEPROM and/or a flash EPROM), one or more holding elements for the actual sensor, at least one plug connection and at least one hole in a base plate through which the sensor is inserted into the tissue of the user, for example by means of an insertion device. Charge-specific sensor data is stored in the storage medium because the sensor and the bodymount, as a disposable, generally form a packaging unit. Furthermore, operating modes can be stored in the storage medium. The sensor is inserted through the hole in the bodymount into the skin by means of an insertion aid. During the insertion, the insertion aid at the same time attaches the sensor, which is provided with a plug, to the bodymount such that the bodymount situated on the body is now provided with two fixed plug systems, namely a plug for attaching the sensor and a plug for attaching the reusable. The insertion aid is once again removed after the insertion. Liquid, for example blood or interstitial fluid, which emerges during the process and thereafter, can be removed by a swab. The so-called reusable is subsequently plugged on and affixed. The reusable has two sockets corresponding to the bodymount couplings. An electrical connection to the battery, the storage medium and the sensor electrodes is established via these sockets, and the measuring function of the continuous monitoring system is initiated on contact. Apart from the sensor electrodes, this system must generally be galvanically hermetically sealed during operation in order to avoid leakage currents and hence measurement errors.

There are a number of technical challenges in such systems. For example, potentiostatic electrochemical systems may generally only have very small leakage currents, for example at a reference electrode of the sensor, because currents in the picoampere range can chemically disintegrate the reference electrode. If such leakage currents disintegrate the reference electrode, the electrochemical system may fail prematurely. By contrast, leakage currents to or from the work electrode of the electrochemical sensor can lead to unidentifiable measurement errors. It is for this reason that the electrical lines and contacts in the system, with the exception of the individual sensor electrodes, should generally be completely isolated galvanically. This is generally only possible to a certain extent with much isolation complexity in the required current range. Environmentally-dependent interference penetrating the system, such as, for example, moisture, dust, salts or similar environmental influences can cause parasitic leakage currents. Hence, the system should be protected from such environmental influences where possible. However, the plug regions are necessarily accessible in the present concepts and there are often storage conditions that are counter to the requirement of high resistance (for example resistances of more than $10^9$ ohms). Thus, in many cases, the high resistance in principle cannot be ensured over a relatively long period of use without targeted protective measures. Some gradual or imperceptible changes in the resistance conditions during ongoing intended operation can therefore only be determined with great metrological complexity in the case of the present signal magnitudes. However, if error detection were to be incorporated in the sensor interacting with the reusable within the scope of a fail-safe concept, this would lead to unjustified error messages in the case of over-sensitive discrimination, or would be ineffective in the case of insufficient discrimination.

Hence, the problems are generally concentrated on the side of the reusable. As discussed above, known concepts provide for multiple applications or even an application by a number of users. However, this means that the reusable is frequently handled by a user, and this cannot be controlled by the system. By contrast, the problem is less pronounced on the side of the sensor itself because said sensor is generally part of the disposable. This means that constructive precautions allow the sensor to be embodied such that it is only subjected to minimal access by the user. Adverse influences during production, storage and transport can be avoided by controlled processes. By way of example, U.S. Pat. No. 6,360,888 B1, which is incorporated herein by reference, has disclosed a sensor packaging system for storing and transporting a glucose sensor. Provision can also be made for an indicator in this packaging system that monitors the extent to which the sensor is subjected to high temperatures. WO 2006/133305 A2, which is incorporated herein by reference, also discloses protective packaging for an implantable bio sensor. In principle, protective concepts are also known from different fields. For example, U.S. Pat. No. 4,801,271, which is incorporated herein by reference, discloses electrical connections that can briefly be closed using a dummy plug.

By way of example, current concepts provide for the sensor to be inserted into an insertion hollow needle after production and to be sterilized in an outer packaging. As a result, the sensor, including its contact area, is protected from being touched if used as intended. Moreover, moisture, dust and similar environmental influences are excluded during storage and transport by suitable packaging measures.

Thus, the described problems are predominantly on the side of the reusable. It needs to be ensured that the reusable is sufficiently protected from environmental influences after production, during transport, during temporary storage, and while the disposable components are being replaced. Although in principle it would also be possible to sidestep this problem by redefining a reusable as a disposable, this would not be an economical solution to the described problem in the case of large production numbers because the reusable generally contains extensive electronics.

SUMMARY

It would therefore be advantageous to provide measures that avoid the disadvantages of known transcutaneous sensor systems. In particular, the proposed measures should ensure that the reusable is protected during transport, temporary storage and/or while the disposable components are being replaced.

The present invention, in alternative embodiments thereof, provides a protective container, a kit, a sensor device and a method wherein a control part includes at least one coupling assembly, the coupling assembly having a sensor coupling for connection with a transcutaneous sensor. The protective container includes a container housing wherein the control part can be held in the container housing with the container housing being adapted to shield the control part from environmental influences and wherein the container includes a connector assembly having at least one sensor connector which seals the at least one sensor coupling in a media-tight fashion when connected thereto. Advantageous further aspects of the invention, which can be implemented individually or in any combination, are also described herein.

In a first embodiment, a protective container is provided for holding a reusable control part of a transcutaneous sensor system for detecting at least one analyte in a bodily fluid. As used herein, a protective container should be understood to be a device having at least one container housing with at least one inner space, into which the control part can be inserted as a whole or in part. In some embodiments, precisely one control part can be inserted into one protective container. However, alternative arrangements in which a plurality of control parts can be inserted into one protective container are also feasible. The container housing, in some embodiments, completely encloses the control part. Alternative embodiments, however, in which the container housing does not completely enclose the control part are also feasible. For example, a housing of the control part itself could form part of the shield for sensitive parts of the control part and be used with a container housing that does not completely enclose the control part. In some embodiments, the protective container can be sealed. For example, the protective container may have a container lid, an opening, a slider or other sealing device such that the inner space can be sealed after the control part has been inserted.

A transcutaneous sensor system, as explained above, should be understood to be a sensor system in which at least one sensor is wholly or partly arranged within body tissue of a human or animal user and in which at least one component of the sensor system is wholly or partly outside of the body tissue, with the at least one component outside of the body tissue, for example the reusable control part, and the sensor being interconnected through the skin or a tissue surface of the user. The interconnection through the skin or tissue surface can be via a wired connection, however, a wireless connection is also possible as an alternative or in addition thereto.

A control part, as explained in more detail below, should be understood to be a component of the transcutaneous sensor system that is designed to actuate the sensor and/or record signals from the sensor and/or evaluate these signals in whole or in part.

As discussed above, the at least one analyte to be detected (with it also being possible for a plurality of analytes to be detected at the same time) can be blood glucose, cholesterol, lactate, triglycerides or combinations of the aforementioned and/or other analytes. Other types of analytes can also be detected, wherein the term analyte can include at least one metabolite, which can be detected qualitatively and/or quantitatively. In principle, any other type of bodily function can also be detected, and so the term analyte detection within the scope of the present invention can generally also comprise any diagnostic functions for registering at least one body state of the user. By way of example, the bodily fluid can be blood, interstitial fluid or other types of bodily fluids.

The control part, which can be inserted into the protective container, should include at least one coupling. In principle, a coupling should be understood to be any interface by means of which the control part can be connected, for example, by wires, to at least one further component. By way of example, the coupling, as will be explained in more detail below, can comprise at least one plug coupling, that is to say a coupling that can be coupled electrically and advantageously mechanically to at least one further component via a plug connection.

The coupling comprises at least one sensor coupling for connecting the control part to at least one transcutaneous sensor. By way of example, this sensor coupling can include a sensor plug. The sensor plug can be a male or female plug and/or include a male and/or a female plug component. However, other embodiments are also possible.

The protective container should have at least one container housing. As described above, the container housing can, for example, have at least one wholly or partly closed inner space. By way of example, the container housing can be embodied in a rigid manner, that is to say it is embodied such that it does not change, or only insignificantly changes, its shape under the influence of its own weight. By way of example, the container housing can be made of a plastic and/or a metallic material. By way of example, the container housing can be embodied as a container, a box, or in a similar fashion, and can comprise one or more container housing components. It should be possible to hold the control part in the container housing. By way of example, the container housing, as described above, can for this purpose include one or more wholly or partly closed inner spaces, into which the control part can be inserted in whole or in part. The container housing is designed to shield the control part from environmental influences. As used herein, shielding is understood to mean a delay of the ingress of environmental influences to the control part, advantageously a complete separation from these environmental influences. More particularly, the ingress of environmental influences to the control part through the container housing can be slowed by at least a factor of 10, advantageously by at least a factor of 100, and particularly advantageously by at least a factor of 1000. Environmental influences can be in the form of dust, dirt, moisture, or combinations of the aforementioned and/or other types of environmental influences which can affect the at least one coupling. Accordingly, there can be complete shielding such that the entire control part is shielded from the environmental influences, with, a partial shielding also being possible. In the case of a partial shielding, the container housing can, be embodied such that it at least shields the at least one coupling from environmental influences. However, it is particularly advantageous for the container housing to surround the entire control part completely and shield it hermetically against environmental influences.

The container housing may also include at least one connector. A connector should be understood to be an element that can be connected, at least mechanically and advantageously electrically as well, to the at least one coupling. It is advantageous to connect the connector to the coupling and seal the latter in a media-tight fashion. Here, sealing in a media-tight fashion should be understood to mean closing the connector such that ingress of media such as dust and moisture is at least significantly slowed down compared to an open coupling, advantageously by at least a factor of 10, more particularly by at least a factor of 100 and particularly advantageously by at least a factor of 1000. Accordingly, as will be explained in more detail below, the connector can comprise at least one plug connector which can be connected to the coupling and seals the latter such that the media cannot ingress into the coupling.

In some embodiments, the control part coupling includes at least the at least one sensor coupling for connecting the control part to the at least one transcutaneous sensor. Moreover, the control part coupling can also include at least one further coupling, for example a control coupling for connecting the control part to at least one control component which can be a disposable control component. As will be explained in more detail below, this allows a measurement system for detecting at least one analyte in a bodily fluid to have at least one reusable control part, at least one transcutaneous sensor, and at least one disposable control component. In the assembled state, the control component can, for example, be mechanically coupled to the transcutaneous sensor. Furthermore, in the assembled state of the measurement system, the control component can include at least one data storage medium, for example a data storage medium for storing characteristic data from the transcutaneous sensor such as charge information and/or calibration data. By way of example, this allows the at least one control component and the transcutaneous sensor to be stored and supplied together as a disposable component. The disposable component formed by the disposable control component and transcutaneous sensor can subsequently be connected to a reusable control part to form a measurement system. The at least one data storage medium can be a volatile and/or a non-volatile data storage medium. As an alternative or in addition to the data storage medium, the control component can also include at least one electrical energy supply, more particularly an electrical energy storage device, for example at least one battery and/or at least one rechargeable battery. Accordingly, the control part can be provided with electrical energy by the control component, wherein the energy is provided, for example, via the control coupling.

If the coupling contains at least one control coupling and at least one sensor coupling, then the connector can have at least one sensor connector for connection to the sensor coupling and, advantageously, for sealing the sensor coupling in a media-tight fashion, and, furthermore, at least one control connector for connection to the control coupling and, advantageously, for sealing the control coupling in a media-tight fashion. The control coupling and the sensor coupling, or the control connector and the sensor connector, are advantageously embodied as separate components. For example, they may be separate plug components or separate plug connectors. However, the control coupling and sensor coupling and/or the control connector and sensor connector can also be wholly or partly combined.

More particularly, the connector can be connected to the coupling while the control part is inserted into the protective container. This means that during the insertion of the control part into the protective container, the connection, for example a plug connection, between the connector and the coupling can be established at the same time. For example, the control part can be plugged into the protective container, for example an inner space of the container housing, with the connection between the connector and the coupling being established at the same time as the control part is plugged into the inner space of the container housing. However, alternative embodiments are also possible.

As explained above, the protective container can provide a moisture-tight shield for the control part wholly or partly introduced into the protective container, that is to say for the whole control part or merely part of the control part. More particularly, provision can be made for a moisture-tight shield for the at least one coupling. On the one hand, a connector can be provided in order to provide this shield. On the other hand, the protective container, more particularly the container housing, can include at least one closure, for example at least one lid and/or at least one slider, which can be sealed after the control part has been introduced into the inner space of the container housing. Moisture-tight shielding should be understood to mean that an ingress of moisture, more particularly an ingress of moisture to the at least one coupling, is significantly slowed-down compared to a non-shielded state, for example by at least a factor of 10, advantageously by at least a factor of 100 and particularly advantageously by at least a factor of 1000. As explained above, the container housing can be produced, at least in part, from a plastics and/or a metallic material. The container housing can also have complete or partial electrical shielding properties, for example shielding from electromagnetic radiation and/or from strong electrical and/or magnetic fields. By way of example, provision can be made for a shielding by at least a factor of 10, advantageously by at least a factor of 100 and particularly advantageously by at least a factor of 1000. The shielding can be brought about by at least one metallic shield in the container housing. For example, conducting materials can be used for shielding. Alternatively, or in addition thereto, provision can also be made for a soft-magnetic shielding.

Furthermore, the protective container can also include at least one desiccant for reducing moisture in the inner space of the protective container. The desiccant can, for example, be introduced as a separate element into the inner space and/or into a space adjoining the inner space. Alternatively, or in addition thereto, the desiccant can be wholly or partly integrated into the container wall. Conventional desiccants can be used as a desiccant, such as, for example, silica gel or other desiccants known, for example, for storing sensitive components such as sensor components.

Alternatively, or in addition thereto, the protective container can also include at least one germicidal means, more particularly a biocide and/or a fungicide. By way of example, this germicidal means, which can in principle kill germs at any stage of their development, can be introduced into the inner space and/or into a space adjoining the inner space as a separate means, for example as a disinfection mean. Alternatively, or in addition thereto, the germicidal means can also be wholly or partly integrated into the protective container, for example the container housing. Thus, for example, germicidal materials, such as silver iodide can be contained as filler in plastics of the container wall.

As explained above, the control part can, in some embodiments, be plugged into the protective container. For such embodiments, the connector can be designed to be connected to the coupling with a plug connection. More particularly, this plug connection can be established when plugging the control part into the protective container. As an alternative, the plug connection can be established separately, for example before or after the plugging the control part into the protective container by separately connecting the coupling to the connector. When the plug connection is being established, the sensor coupling can be connected to the sensor connector by a plug connection, and the control connector can optionally be connected to the control coupling by a plug connection.

As discussed above, the connector is designed to be connected to the coupling and to seal the latter in a media-tight fashion. Accordingly, the connector can have at least one O-ring seal. Thus, for example, the sensor connector can have an O-ring seal, and the control connector can optionally likewise have an O-ring seal. In general, the protective container can be designed to lubricate the connection between the connector and the coupling. By way of example, provision can be made for an automated O-ring lubrication to prevent the at least one optional O-ring drying out by lubricating it at regular or irregular intervals. By way of example, a lubricant that is advantageously compatible with electronic components and biologically harmless can be used for this purpose. The lubricant is advantageously hydrophobic in order to prevent a moisture film in the plug region below the O-ring.

As explained above, the connector is first of all designed to seal the coupling in a media-tight fashion when the former is connected to the coupling. The connector can optionally establish an electrical connection to the coupling. Thus, for example, the sensor connector can establish an electrical connection to contacts on the sensor coupling and the control connector can optionally establish an electrical connection to one or more contacts on the control coupling. Accordingly, the connector can, for example wholly or partly, be designed as an electrical plug, by means of which one or more contacts on the coupling can be contacted electrically in addition to the above-described media-tight closure function.

In particular, the connector can be designed to provide ESD protection for the control part. As used herein, ESD protection should be understood to mean protection from destruction by electrostatic discharges. By way of example, the sensor connector can be designed to provide ESD protection at the sensor coupling. Alternatively, or in addition thereto, the control connector, which can optionally be provided, can be designed to provide ESD protection at the control coupling.

The ESD protection can be ensured in a number of different ways which are known to a person skilled in the art. By way of example, the coupling can have at least two contacts- and the sensor coupling can have at least two, advantageously three or more contacts. Alternatively, or in addition thereto, the control coupling can have one, two or more contacts. The connector can be designed to interconnect the at least two contacts, for example the at least two contacts of the sensor coupling and/or the at least two contacts of the control coupling via at least one of the following elements: at least one ohmic resistor; at least one diode; at least one capacitor. By way of example, the sensor coupling can have two or three contacts, namely one contact for a work electrode and in each case at least one contact for a reference electrode and a counter electrode. In this case, the reference electrode and the counter electrode can be designed separately, like their contacts as well, but in principle they can also be combined such that their contacts can also be combined. In this case, the contact of the counter electrode can, for example, be connected to the contact of the reference electrode, for example via one or more of the aforementioned elements, and the contact of the reference electrode and of the work electrode can be interconnected, for example via one or more of the aforementioned elements. Other ESD protective circuits are also possible, for example by grounding one or more contacts.

As discussed above, the protective container can be embodied as a purely passive protective container. Accordingly, the protective container can, for example, provide a purely media-tight closure for the coupling. The protective container can optionally provide ESD protection for the control part as explained above. Optionally, active functions may additionally be integrated into the protective container, for example one or more active electrical and/or logical functions. More particularly, the protective container can be designed to undertake a function test of the control part. For this purpose, the protective container can, for example, be designed to supply at least one test current and/or at least one test voltage to the coupling and more particularly the sensor coupling. By way of example, the protective container can then be designed to retrieve at least one signal generated by the control part, more particularly a measurement signal and/or a measurement result. To this end, a supply voltage is advantageously provided to the control part by the protective container, for example via the control coupling. More particularly, this retrieval can be undertaken wirelessly, for example by a telemetry component of the control part, that is to say a component embodied for wireless communication (for example radio communication) between the control part and another instrument, for example a data manager. The protective container can be designed to communicate at least one result of the function test to at least one further instrument and/or to at least one user. By way of example, the at least one further instrument can include one or more of the following instruments: a data manager, which is connected to the protective container by means of at least one wired or wireless connection, for managing measurement results from the transcutaneous sensor system; a computer, more particularly a medical practitioner's computer and/or a patient's computer, connected to the protective container by a wired or wireless connection; a computer network; a mobile communication instrument such as, for example, a cellular phone or a personal digital assistant (PDA). Alternatively, or in addition thereto, further instruments can also be utilized.

The protective container can be designed to transmit a result of the function test to a user via at least one user interface. More particularly, this user interface can include at least one indicator element. This indicator element can include, for example, a display, an illuminated indicator, an acoustic indicator, a haptic indicator or combinations of the aforementioned and/or other indicator elements.

By way of example, the function test can involve collecting data. Such function tests can be carried out at regular intervals and can be stored in the protective container. The results from the function tests can, for example, be communicated to another instrument and/or to a user and/or differently, as explained in the present disclosure.

In one embodiment, the protective container can be designed to undertake a leakage-current measurement during the function test between at least two contacts on the coupling. Such a leakage-current measurement may be between at least two contacts on the sensor coupling and/or on the control coupling. By way of example, a technical defect and/or contamination can be inferred if a measured leakage current exceeds one or more tolerance thresholds. A leakage current is a current between at least two contacts or test sites, between which, ideally, there should be a very high resistance ($>10^{12}$ ohm).

The protective container can also be designed to retrieve at least one signal, more particularly a measurement signal and/or a measurement result, which is generated by the control part. This retrieval can be performed during the function test and/or can be part of the function test, for example during the aforementioned leakage-current measurement. Alternatively, or in addition thereto, such a retrieval can be performed during the supply of the at least one test current.

The protective container can also be designed to transmit at least one result of the function test to at least one additional instrument and/or one user. By way of example, this transmission can be brought about by providing the protective container with at least one interface. By way of example, a user interface can be provided for informing the user about the result of the function test. This user interface can comprise at least one indicator element, for example at least one display and/or an illuminated indicator and/or another type of visual indicator and/or an acoustic indicator and/or a haptic indicator element. Alternatively, or in addition thereto, the interface to a user and/or another instrument can comprise one or more of the following interfaces: a unidirectional data interface, a bidirectional data interface, an indicator element for visually indicating at least one item of information, more particularly a display and/or an illuminated indicator; an indicator element for acoustically outputting at least one item of information; an indicator element for haptically outputting at least one item of information; at least one operating element for entering an item of information and/or a control command, for example at least one enter key. The at least one optional data interface can, for example, comprise a wired or wireless data interface. By way of example, use can be made of infrared data interfaces, USB data interfaces, serial interfaces or other types of interfaces as are known by a person skilled in the art.

The protective container can furthermore be designed to store the data from the function test. For this purpose, the protective container can, for example, include at least one storage element. Alternatively, or in addition thereto, the protective container can have its own intelligence. Accordingly, the protective container can, for example, have a data-processing instrument, more particularly at least one microcontroller, which can include input and output elements and, optionally, one or more storage media. By way of example, the data-processing instrument can control or at least support the above-described function test in one or more of the described embodiments.

The protective container can furthermore be designed to transmit an alert to a user and/or a further instrument if a fault is established in the control part during the function test. As used herein, an alert should be understood to be any information relating to a fault, which can, for example, consist of a warning signal and/or differently designed warning information, for example an error bit in the data transfer. A fault should, for example, be understood to mean a deviation of measurement results in the function test from predefined intended ranges and/or intended values, for example overshooting and/or undershooting certain thresholds.

The protective container can also have at least one electrical energy supply. By way of example, this electrical energy supply can be used to provide electrical energy to the control part inserted into the protective container. Alternatively, or in addition thereto, the energy supply can feed components of the protective container itself, for example the aforementioned optional data-processing instrument and/or the aforementioned optional interface. The electrical energy supply can include one or more of the following energy supplies: an internal energy supply, in particular at least one internal energy storage device, more particularly at least one battery and/or at least one rechargeable battery; a coupling for an external energy supply, more particularly a mains plug and/or a mains connection.

The protective container can furthermore be incorporated into the measurement concept of the transcutaneous sensor system. Thus, the protective container can, for example, be designed to receive at least one item of calibration information, more particularly an item of calibration information from an external measurement instrument for detecting the at least one analyte by means of at least one test element. Such a measurement device for detecting the at least one analyte by means of at least one test element can alternatively also be integrated into the protective container itself. The protective container can be designed to pass on the calibration information to the control part, for example via the at least one coupling. Exemplary embodiments will be explained in more detail below.

A kit is also disclosed in addition to the protective container. This kit comprises at least one protective container in one or more of the above-described embodiments and furthermore comprises at least one reusable control part of a transcutaneous sensor system for detecting at least one analyte in a bodily fluid. By way of example, the control part can correspond to the embodiments relating to the control part illustrated above. Accordingly, the control part comprises at least one coupling, which in turn has at least one sensor coupling for connection to at least one transcutaneous sensor and, optionally, at least one control coupling for connecting the control part to at least one control component, more particularly at least one disposable control component.

The control part can furthermore comprise at least one of the following elements: a data-processing instrument, more particularly a microcontroller; a data storage medium; evaluation electronics for actuating and/or evaluating the at least one transcutaneous sensor; a unidirectional and/or bidirectional interface for interchanging data, more particularly measurement data, with at least one further instrument, for example with at least one data manager, more particularly a wireless interface, more particularly a telemetry component. In respect of further possible embodiments of the reusable control element, reference can, for example, be made to the prior art cited above, in particular to US Pub. No. 2008/0242962 A1 which is incorporated herein by reference. More particularly, the control part can correspond to the reusable base station described therein. However, alternative embodiments are also possible. In some embodiments, the control part is designed to be provided with electrical energy via the coupling, for example, the control coupling. For example electrical energy may be provided from an energy supply of the protective container, for example an energy storage device of the protective container. Accordingly, the control part may, for example, not include its own internal energy supply, more particularly its own energy storage device.

According to a further aspect of the present invention, a sensor device is disclosed for detecting at least one analyte in a bodily fluid. This sensor device comprises at least one transcutaneous sensor, wherein the transcutaneous sensor can at least be partly implanted into a body tissue. Hence, implantability should be understood to be a property with which at least part of the transcutaneous sensor can be introduced into a body tissue, for example an interstitial tissue. In the process, other regions of the sensor may protrude out of the body tissue and, for example, may be guided to the outside through the skin of a patient. By way of example, implantability can be ensured by the use of biocompatible materials for the region of the transcutaneous sensor to be implanted. For example, the implantable sensor can use materials that have biocompatible properties or are coated by biocompatible materials such that ingress of non-biocompatible materials and/or direct contact between non-biocompatible materials and body tissue and/or bodily fluids can be prevented.

In principle, the transcutaneous sensor can be based on any sensor principle for detecting the at least one analyte. By way of example, the sensor can have at least one sensor material that specifically changes at least one property that can be detected physically and/or chemically when the at least one analyte to be detected is present. "Specific" in this case should be understood to mean that this property advantageously only occurs in the presence of the analyte to be detected, and possibly in chemically very similar analytes, but not in the presence of other materials or merely in the presence of materials whose occurrence in the bodily fluid is very unlikely. As explained above, the at least one property to be detected can, for example, be an electrochemical property. Accordingly, the sensor can, for example, be an electrochemical sensor or comprise an electrochemical sensor. By way of example, the sensor can, for this purpose, comprise at least one work electrode and/or at least one counter electrode and/or at least one reference electrode. The at least one work electrode can be coated with at least one detection chemical, for example at least one detection chemical that comprises at least one enzyme and/or at least one mediator. By way of example, the enzyme can comprise glucose oxidase or glucose dehydrogenase. Such transcutaneous sensor systems are known to a person skilled in the art. Detection of the at least one analyte can, for example, be brought about by means of a known potentiostatic measurement, by means of which, the electrode potential of the counter electrode is regulated with respect to the work electrode, wherein the potential of the reference electrode is the reference for regulating the counter electrode. The current generated proportionally to the glucose concentration or, generally, to the analyte concentration by the work electrode can be evaluated as a measurement variable.

The sensor device may also include a kit that includes one or more of the above-described embodiments, that is to say at least one reusable control part and at least one protective container.

The sensor device can also include at least one control component. The control component can be embodied as a disposable control component or at least comprise a disposable control component. However, alternatively, or in addition thereto, a reusable control component is also possible. By way of example, it may be possible to connect the control component to the sensor in a mechanical and/or electrical fashion. By way of example, the control component can comprise one or more of the following components: an electrical energy supply, more particularly an integrated electrical energy storage device, advantageously at least one battery and/or at least one rechargeable battery; a data storage element, more particularly a non-volatile data storage element, for example an EEPROM and/or a flash-EPROM. As mentioned above, the control component may have a conventional design known in the art. Thus, by way of example, the control component may be embodied as per the sensor carrier unit in US Pub. No. 2008/0242962 A1, which is incorporated herein by reference and so reference may be made to this document in respect of possible details of this control component. However, other embodiments are also possible.

A conceptual distinction should be made between the actual transcutaneous sensor, the control part, the control component, the protective container, the sensor device and the transcutaneous sensor system. In particular, these elements can be embodied individually or overall as independently manageable elements, more particularly as separately designed elements, which can, for example, be produced, stored, packaged and transported independently of each other. A transcutaneous sensor system represents a unit by means of which the measurements can actually be carried out. The transcutaneous sensor system thus comprises the transcutaneous sensor, the control part and, optionally, the control component. As described above, during the operation of the transcutaneous sensor system, the reusable control part is or can be connected to the transcutaneous sensor via the sensor coupling and to the control component via the control coupling. Thus, all three components together form a unit that is referred to as a transcutaneous sensor system. Conceptually, this transcutaneous sensor system should be distinguished from the above-described sensor device, which comprises the kit with the protective container and the control part and, furthermore, at least one transcutaneous sensor and, optionally, the control component that can be connected to the sensor.

A method for protecting a reusable control part of a transcutaneous sensor system for detecting at least one analyte in a bodily fluid is proposed in a further aspect of the present invention. The control part comprises at least one coupling with at least one sensor coupling for connection to at least one transcutaneous sensor, and optionally at least one control coupling for connecting the control part to at least one control component which may be a disposable control component. In the method, the control part is isolated from the transcutaneous sensor and shielded from environmental influences and the coupling is sealed in a media-tight fashion. The closure can provide a purely mechanical closure for protection against the ingress of environmental influences, such as, for example, dust or moisture. Optionally, the closure can provide ESD protection. Once again, alternatively, or in addition thereto, the closure can perform a function test. Sealing can take place using a protective container with a variety of different closures.

The above-described devices and methods have a number of advantages over known devices and methods. In particular, malfunctions caused by contamination of a reusable control part can be effectively avoided, or at least reduced. The protective container can be designed as a portable protective container and can, for example, be carried by a user in a jacket pocket, or can be part of a portable set of accessories. The described option of incorporating function tests in the protective container allows the protective container to be part of an overall fail-safe concept and can thus effectively contribute to increasing the user-friendliness and to increasing the reliability of the sensor device and the transcutaneous sensor system.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Figure 1:
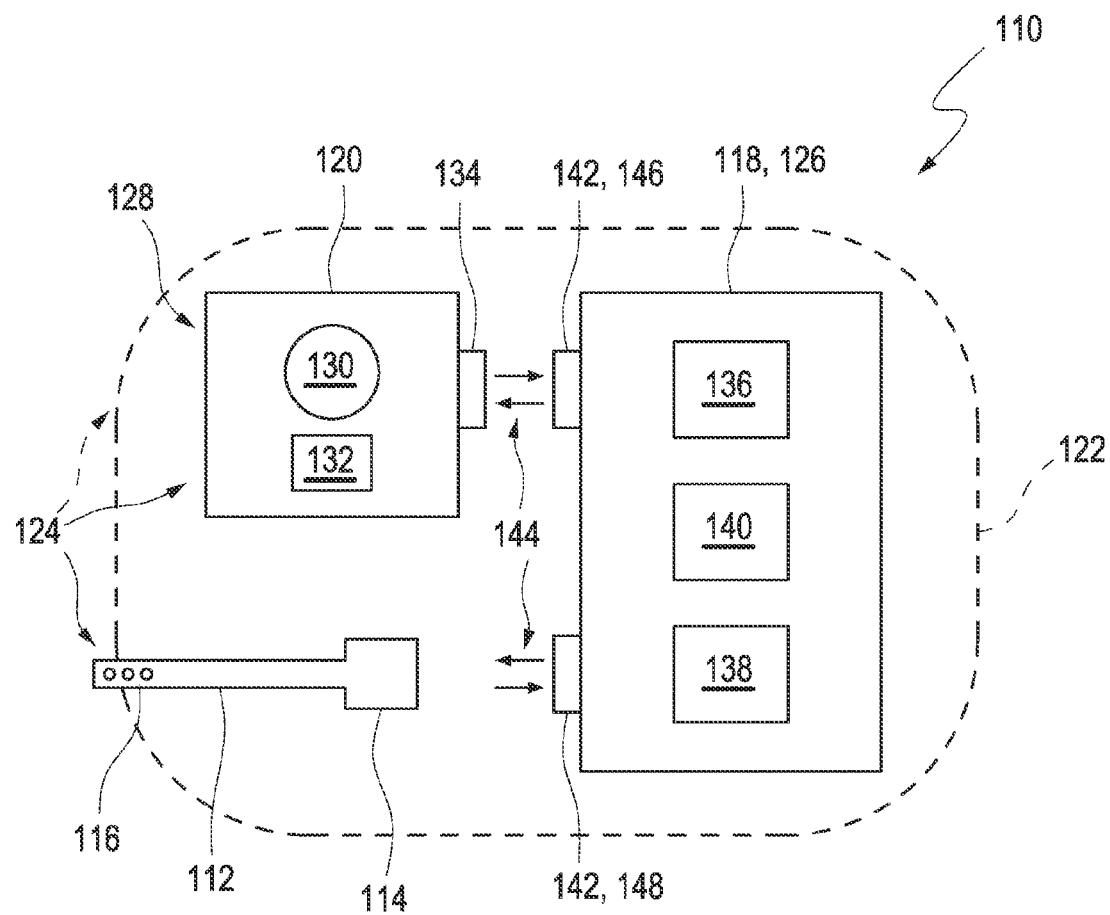
FIG. 1 is a schematic illustration of a transcutaneous sensor system.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of the present invention.

FIG. 1 schematically illustrates, in an exemplary fashion, an embodiment of a transcutaneous sensor system 110 for detecting at least one analyte in a bodily fluid. By way of example, the transcutaneous sensor system 110 in the illustrated embodiment can correspond to the transcutaneous sensor system described in US Pat. Pub. No. 2008/0242962 A1 which is incorporated herein by reference. In the illustrated exemplary embodiment, the transcutaneous sensor system 110 comprises a transcutaneous sensor 112 with a sensor plug 114 and a sensor region 116 that can be introduced into the body tissue. The transcutaneous sensor system 110 also includes a reusable control part 118 and a control component 120, more particularly a disposable control component. The disposable control component can be designed for a single use, for example, for merely a single measurement period. However, other control component designs may also be employed. The control component 120, the transcutaneous sensor 112 and an attachment element 122, such as a plaster for adhesion onto a skin surface, and, if necessary, further components such as, for example, housing components, together form a so-called disposable 124. The disposable 124 is a disposable part, whereas the reusable control part 118 forms a so-called reusable, that is to say, a reusable part. The control component 120 is often also referred to as a bodymount 128.

In the illustrated embodiment, the control component 120 comprises an electrical energy storage device 130 and/or a data storage medium 132 in an exemplary fashion. By way of example, the data storage medium 132 can be designed as a non-volatile data storage medium, for example as a ROM and/or an EEPROM and/or a flash EPROM. In the illustrated embodiment, the control component 120 also includes a control plug 134.

In the illustrated embodiment, the reusable control part 118, in turn, comprises a data-processing device in the form of a microcontroller 136, actuation and evaluation electronics 138 for actuating the transcutaneous sensor 112, and a telemetry component 140 for wireless communication of measurement results. The telemetry component 140 can communicate, for example, with a data manager (not illustrated in FIG. 1), which likewise can optionally be a component of the transcutaneous sensor system 110. Furthermore, the reusable control part 118 can also include one or more storage media, which can also be volatile storage media and/or non-volatile storage media. Whereas the data storage medium 132 in the control component 120 is advantageously used for permanently storing charge information relating to the sensor element 112, for example, producer-specific and/or production-specific information, such as calibration information, the data storage medium of the reusable control part 118, which can, for example, be a component of the microcontroller 136, can be used for storing measurement results, which can subsequently be transmitted to the data manager via the telemetry component 140.

Accordingly, the reusable control part 118 can comprise at least one coupling assembly 142, which has an exemplary two-part design in this embodiment and can form a plug connection 144 or another type of connection. In the illustrated embodiment, the coupling assembly 142 comprises a control coupling 146 for connecting it to the control plug 134 and a sensor coupling 148 for connection to the sensor plug 114. Alternative embodiments are also possible.

FIGS. 2 to 5 show various perspective views of components of the transcutaneous sensor system 110 of FIG. 1. These components are discussed below.

Figure 2:
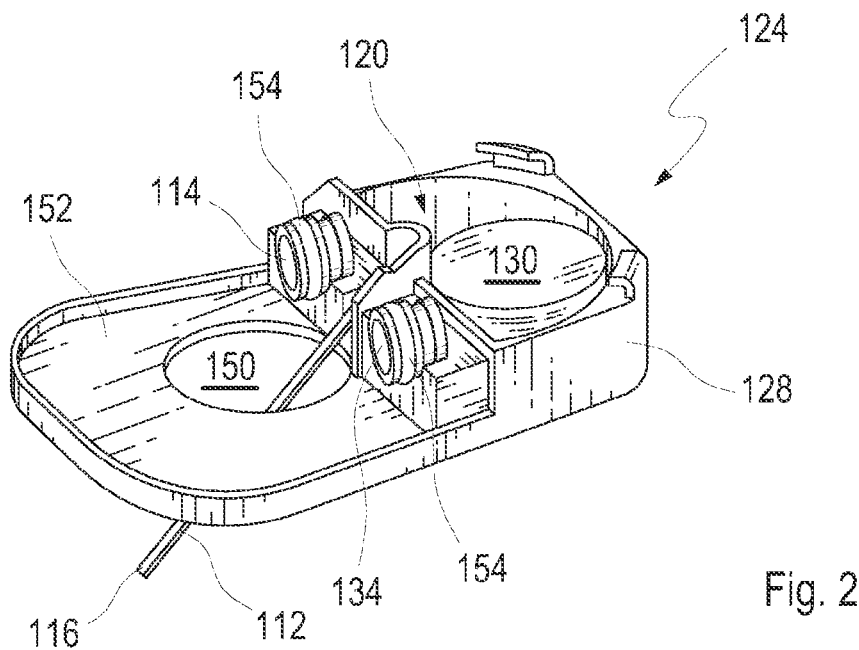
FIG. 2 is a perspective view of a disposable part of a transcutaneous sensor system.

FIG. 2 is a perspective view of a bodymount 128 without the attachment element 122 but with mounted transcutaneous sensor 112. This illustration shows that the transcutaneous sensor 112 can be guided through a hole 150 in a base plate 152 such that the sensor region 116 projects into a body tissue of a user. This perspective illustration also shows that the sensor plug 114 and the control plug 134 can each include optional sealing elements 154, for example O-rings.

Figure 3:
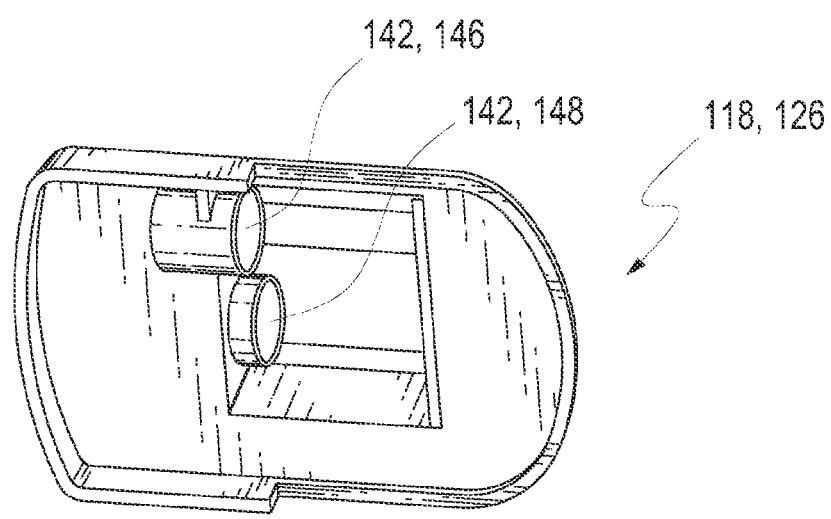
FIG. 3 is a perspective view of a reusable of a transcutaneous sensor system.

FIG. 3 shows a perspective view of an exemplary embodiment of the reusable control part 118, in a view from below. The control coupling 146 and the sensor coupling 148 can be identified in this illustration. By way of example, in order to establish the plug connection 144 of FIG. 1, active plug elements, for example, spring-loaded elements, can be arranged only on the side of the reusable 126, that is to say of the control part 118.

Figure 4:
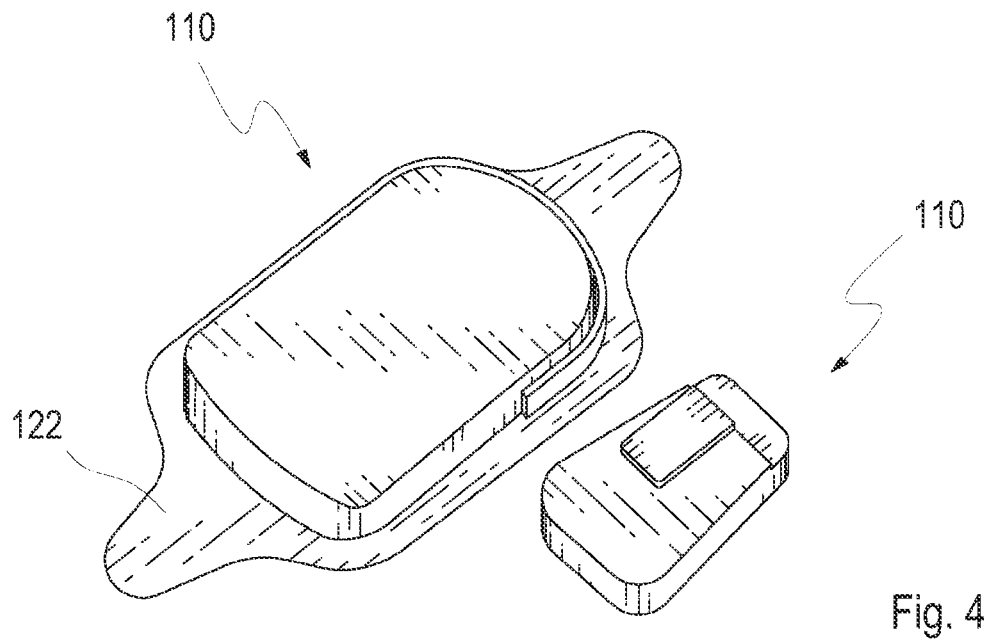
FIG. 4 is a perspective view of two exemplary embodiments of transcutaneous sensor systems.
Figure 5:
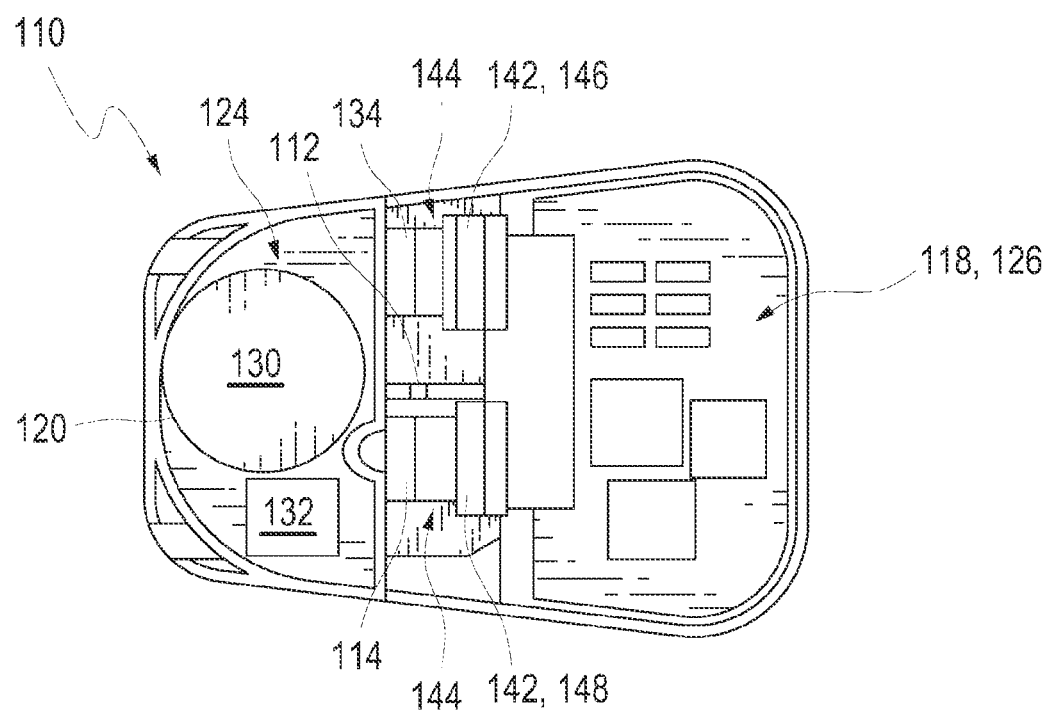
FIG. 5 is a plan view of a transcutaneous sensor system with a removed lid.

The complete transcutaneous sensor system 110 is once again illustrated in FIG. 4 in two different exemplary embodiments. FIG. 5 illustrates the complete transcutaneous sensor system 110 with an opened housing. In FIG. 5, the control component 120, the reusable control part 118 and the coupling 142 can be clearly seen in the connected state. The disposable 124 can include all of the parts that are used for only one measurement cycle, that is to say the sensor 112, the bodymount 128 without the reusable 126 and, if necessary, an insertion needle (not illustrated in FIG. 5). The entire functional unit of the transcutaneous sensor system 110 with sensor 112, bodymount 128 and reusable 126 is often also referred to as a "patch."

The passive parts of the plug connection 144 in FIG. 5, for example, conductor tracks, can be located entirely within the bodymount 128. That part of the disposable 124 up to the plug connection 144 is illustrated in an opened-up fashion in FIG. 5, that is to say that part to the left of the plug connection 144 in FIG. 5. This part can be hermetically sealed, for example by a lacquer, a seal and/or a cast. This extends the hermetic galvanic isolation of the electrical circuit found in the reusable 126. The sealing elements 154, for example the O-rings, can ensure that, during error-free operation, the transcutaneous sensor system 110 only permits an electrical current between the electrodes of the sensor region 116, and there only between a work electrode and a counter electrode.

Figure 6:
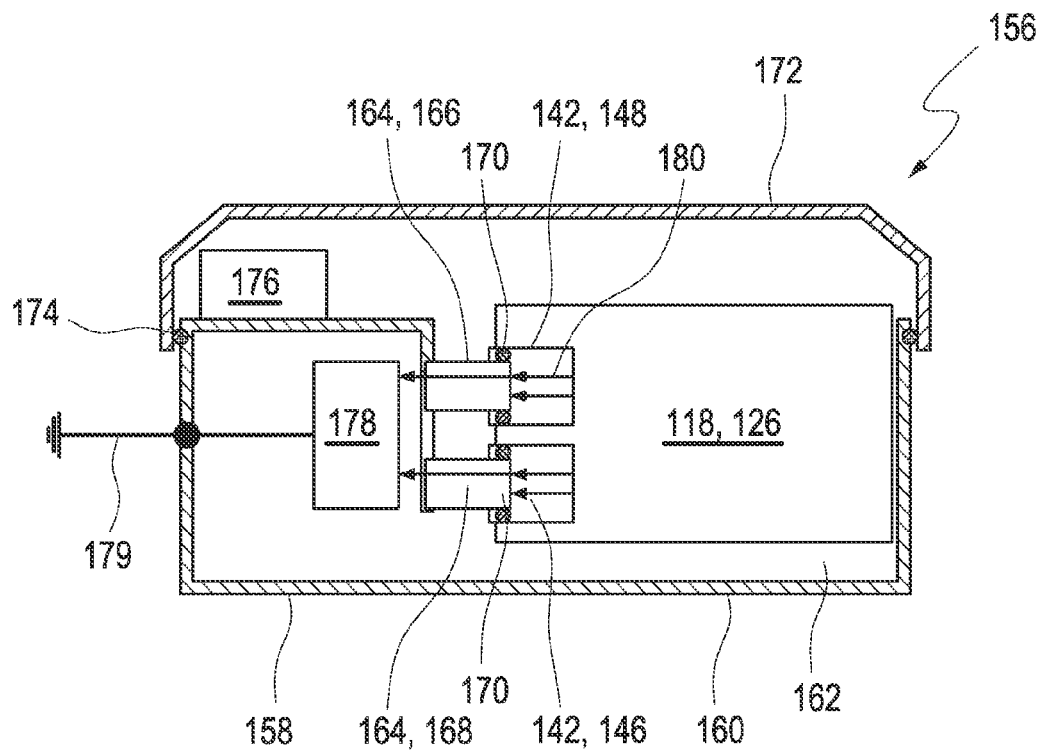
FIG. 6 is a schematic cross sectional view of an exemplary embodiment of a kit with a protective container and a reusable control part.
Figure 8:
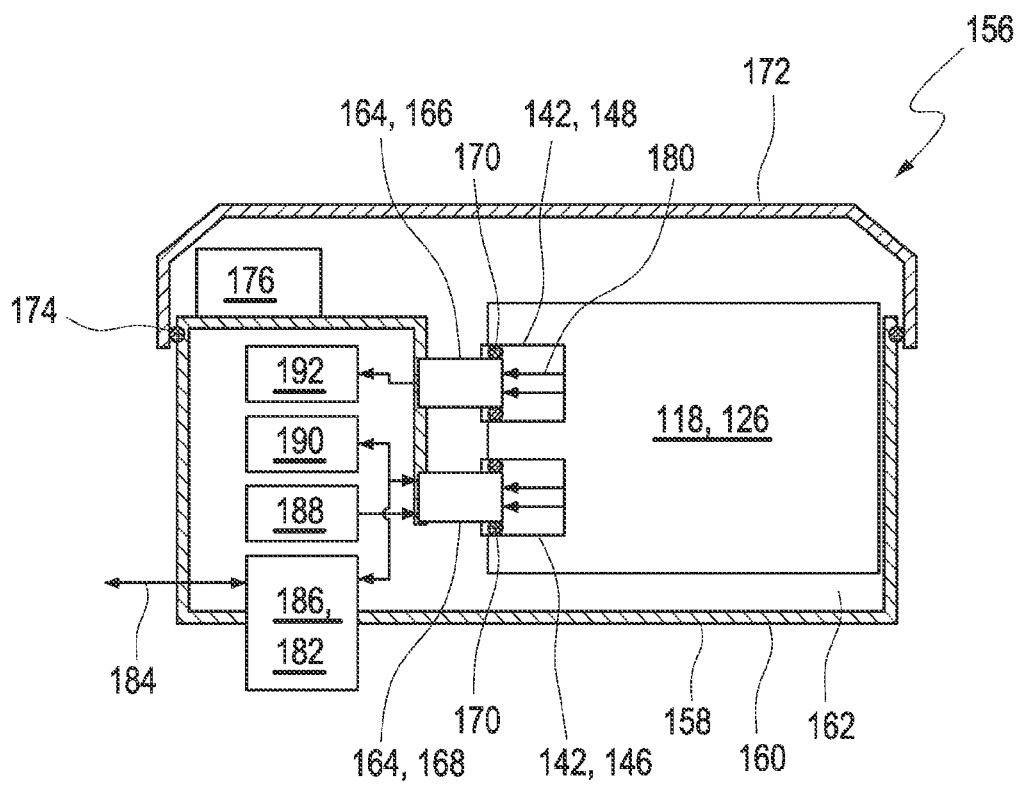
FIG. 8 is a schematic cross sectional view of an alternative embodiment of a kit with a protective container and reusable control part.

FIGS. 6 and 8 illustrate different exemplary embodiments of a kit 156. Kit 156 includes the reusable control part 118 in the form of the reusable 126 and a protective container storage container and includes a container housing 160 with an inner space 162 in which the reusable control part 118 can be positioned or held.

The protective container 158 also includes at least one connector assembly 164 for connection to the coupling assembly 142. In the illustrated exemplary embodiment, the connector assembly 164 comprises a sensor connector 166 for establishing a connection to the sensor coupling 148 and, optionally, a control connector 168 for connection to the control coupling 146 of the reusable 126. The connectors 166, 168 can, for example, be designed as closure plugs and can be embodied with one or more sealing elements 170. Sealing elements 170 may, for example, be O-rings. The connector assembly 164 can seal the coupling assembly 142 in a media-tight fashion in this or in another fashion. Furthermore, the protective container 158 can have a closure element 172, for example a box lid or other type of closure element, wherein this closure element 172 can have one or more additional sealing elements 174, for example a box seal. Sealing elements 174 can seal the inner space 162 within the container housing 160, for example within the box chassis, against environmental influences, advantageously against humidity, dust, contaminants or similar environmental influences. Furthermore, the container housing 160 can provide magnetic, electromagnetic or electrical shielding. Additionally, at least one desiccant 176 can be housed in the container housing 160 in order to reduce the humidity within the inner space 162.

The protective container 158 can be embodied with various additional functionalities for the reusable 126 when it is stored between the individual deployment intervals. The protective container 158 can thereby be used under various operating conditions. Thus, for example, the protective container 158 can be adapted for use under following operating conditions:

Individual user, permanent monitoring: In this operating condition, advantageously up to 52 transcutaneous sensors 112 are successively used and worn, quasi-permanently, by one and the same user by means of one reusable 126.

Individual user, sporadic use: In this case, the user uses a reusable 126 in combination with only a few transcutaneous sensors 112 on their own body. Weeks to months can separate the episodes of usage. Advantageously, the usage should not last for more than 1 year for reasons of hygiene.

Multiple users: A reusable 126 is applied to different users by qualified staff in a clinic or another institution. The usage frequency can vary between seldom and frequent, but, advantageously, 52 uses and/or an operating duration of 1 year should not be exceeded.

Further usage scenarios are also feasible. In most cases, an important function of the protective container 158 is to protect the coupling assembly 142 on the side of the reusable 126 from the ingress of dust, salts and moisture, irrespective of the selected operating scenario. The most critical case with regard to moisture is the ingress of water vapor. By contrast, in most cases ingress of dripping water and splashed water is unlikely to be encountered during the storage phase when the apparatus is used as intended.

The protective container 158 can also be designed to avoid or at least to reduce electrostatic discharge (ESD) and, hence, possible damage during storage and/or removal. This is illustrated in an exemplary fashion in FIG. 6. In some embodiments, the protective container 158 has only passive functions. In addition to keeping the inner space 162 and/or the coupling 142 dry, alternatively, or in addition thereto, the protective container 158 con provide contact protection, a biocidal and/or fungicidal function, protection against electric charging, for example in the form of a conductive coating of container housing 160 and/or closure element 172, or combinations of the aforementioned and/or other functions. By way of example, the biocidal and/or fungicidal function can be implemented by using at least one biocide and/or fungicide, which can be wholly or partly incorporated and/or integrated into the container housing 160. The biocides and/or fungicides should be selected such that they have no negative influence on the so-called biocompatibility. Furthermore, ESD protection 178 can be provided for the coupling 172, that is to say for the control coupling 146 and/or the sensor coupling 148. By way of example, the control coupling 146 and/or the sensor coupling 148 can include one or more contacts 180 for which ESD protection 178 can be provided. This is illustrated in an exemplary fashion in FIG. 7 for contacts 180 of the sensor coupling 148. These contacts 180 can, for example, comprise a contact for a work electrode (WE), a contact for a reference electrode (RE) and a contact for a counter electrode (CE).

Figure 7:
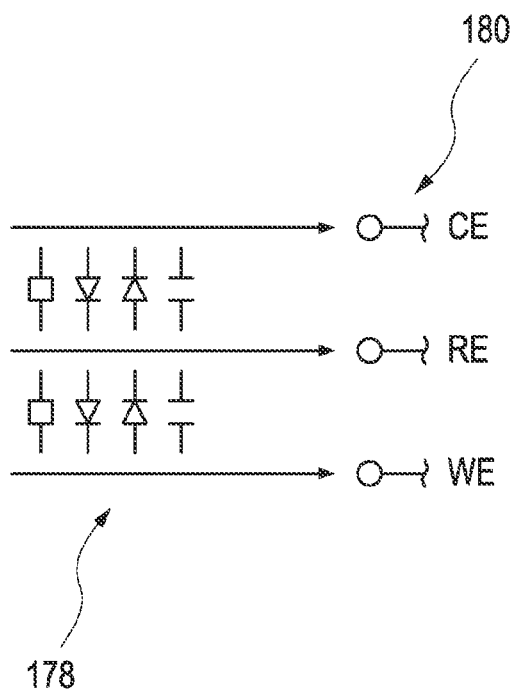
FIG. 7 is a schematic illustration showing the provision of ESD protection.

The contacts for the reference electrode and the counter electrode can be formed separately, or, they can be combined. As shown in FIG. 7, the ESD protection 178 can involve connecting the contacts 180. Thus, for example, the counter electrode and the reference electrode, and also the reference electrode and the work electrode, and optionally the counter electrode and the work electrode too, can be interconnected, for example by ohmic resistors, diodes, capacitors or combinations of the aforementioned and/or other elements. A person skilled in the art will understand the use of such ESD protection 178. Furthermore, provision can be made for suitable compensation devices for electrostatic charge, such as, for example, grounding, discharge networks or the like. Alternatively, or in addition thereto, provision can also be made for at least one grounding and/or electric ground and/or a connection to such elements. This is illustrated in an exemplary fashion in FIG. 6. Thus, for example, the container housing 160 and/or other components of the protective container 158, for example, the at least one optional component for ESD protection 178 (FIG. 6), can be grounded over at least one ground line 179.

Alternatively, or in addition thereto, the protective container 158 can protect the reusable 126 from mechanical influences, such as, for example, impacts, shocks, vibrations or the like, during storage and removal, or at least moderate mechanical effects. Accordingly, cushioning, springs or the like can be provided in the protective container 158.

The protective container 158 can be used for temporary storage of an already used reusable 126. Alternatively, or in addition thereto, the protective container 158 can be used as packaging for a new product. In the process, the protective container 158 and/or the closure element can be adorned with one or more approval marks and/or pictograms relating to use.

In addition to the purely passive approach illustrated in FIG. 6, other embodiments in which the protective container 158 can have additional functionality are also possible. This is illustrated in an exemplary fashion in FIG. 8, wherein not all of the options illustrated in FIG. 8 have to be implemented.

Thus, the protective container 158 can carry out function tests of the reusable 126 automatically, permanently or following a user instruction. The functions of the protective container 158 can also be incorporated in a superordinate fail-safe concept. Accordingly, in the exemplary embodiment shown in FIG. 8, the protective container 158 can include one or more interfaces 182. By way of example, these can comprise interfaces for communication with a user, for example an operating part and/or a display, and/or a data interface 184 and/or one or more operating elements. Furthermore, this can comprise a data-processing device 186, for example a microcontroller. The protective container 158 can alternatively, or in addition thereto, include an energy supply 188. The latter can, for example, have a battery and/or a mains part. Alternatively, or in addition thereto, the protective container 158 can also include one or more data storage media 190. Furthermore, the protective container 158 can include one or more networks 192. These networks can, for example, comprise internal networks and/or external networks, wherein, in the latter case, for example, one or more interfaces can be provided in turn for a connection to these networks. For example, the protective container can include a network interface 192 for connection to the Internet, a medical practitioner's computer, a user computer, an external network, a data manager or another component.

The protective containers 158 as illustrated in FIGS. 6 and 8 and other exemplary embodiments of the protective container, can be controlled not only by the reusable 126 but also by further components in the transcutaneous sensor system 110 or by external components. By way of example, there can be direct communication with a data manager, for example, by radio communication.

The protective container 158 can also support a user in monitoring the reusable 126 with regard to its functionality between directly successive uses after a manual disinfection, for example, a spray disinfection and/or a wipe disinfection. In the case of a malfunction, this saves the user the loss of a disposable 124, including a transcutaneous sensor 112. Furthermore, good venting and/or active air conditioning can be provided for drying.

The protective container 158 can also have a function for defined re-lubrication of the coupling assembly 142, for example of the couplings 146 and/or 148. Trials have shown that the demonstrably best-suited sealing concept by means of O-rings can, without lubrication, lead to stresses in the plug connection 144, which can lead to a poor sealing effect. The O-rings are advantageously on the plugs 114, 134 in the disposable 124. This generally ensures that the O-rings have an optimum shape and optimum elasticity properties every time the disposable/sensor is replaced. By way of example, the O-rings are lubricated in the disposable/sensor production process. However, the sensor coupling 148 and control coupling 146 in the control part 118 can be re-lubricated using suitable reservoirs in the sealing elements 170. Thus, lubricating the O-rings on the disposable side can be dispensed with and, with this, possible unfavorable long-term chemical influences on the sensor properties by the lubricant.

Thus, the protective container 158 can, for example, provide a hermetically sealed box as an embodiment, which box, for example, offers sealing against moisture and/or dust. By way of example, the box can be made of plastics. At least one reusable 126 can be inserted into the protective container 158, for example by insertion or plugging in by a user. In the process, the design of the reusable 126 advantageously avoids having the contacts 180 being touched by the user and thus minimizes the risk of ESD during handling.

As shown in FIG. 6, the sensitive plug region around the coupling assembly 142 can be partly protected. In the process, the coupling assembly 142 on the reusable 126 can be sealed by means of the sealing elements 170, which advantageously correspond to the sealing elements 154 in the transcutaneous sensor system 110.

An optional desiccant 176 can be provided in the protective container 158 and dimensioned for a defined period of time. By way of example, provision can be made for a sufficient amount to establish a defined humidity for a defined period of time, for example, a humidity in the inner space 162 lying below a predefined value of relative humidity.

The materials of the container housing 160 can be biocidal and/or fungicidal. Alternatively, the container housing 160 can itself be cleaned and/or disinfected easily to avoid the spread of germs.

Another embodiment of the protective container 158, which can, for example, be implemented with the exemplary embodiment illustrated in FIG. 8 or a similar "intelligent" embodiment, can provide for the contacts 180 of the reusable 126, more particularly the contacts 180 of the sensor coupling 148, to be connected to a "dummy sensor" in the protective container 158. In such an embodiment, a passive, or an active, sensor can be simulated, for example, in the form of passive impedances and/or in the form of active electronics. Accordingly, the protective container 158 can, for example, comprise a test circuit for connecting the reusable 126 on the box-side and optionally undertake a function test of the control part. By way of example, an active test of the impedance conditions can be carried out in the protective container 158 during storage. For example, such embodiments can aim for discrimination thresholds of approximately ±5%.

As explained above, the transcutaneous sensor system 110 will generally employ the electrical energy storage device 130, for example a battery, and a data storage medium 132, for example an EEPROM or flash EPROM, in the disposable 124 and connect them to the reusable 126 via the control coupling 146 and the control plug 134. When the reusable 126 contacts the disposable 124 or the bodymount 128, the reusable 126 is supplied with voltage, whereupon the latter may initiate the function procedure of the transcutaneous sensor system 110 with a reset. After the initiation, the reusable 126 connects to the data storage medium 132. The reusable 126 can be prompted by external sources to operate in various modes as a result of specific coding of the data storage medium 132. By way of example, provision can be made for a patient mode, a production mode, a programming mode or a test mode. If an appropriately programmed data storage medium 132 is integrated into the protective container 158, the reusable 126 would immediately enter the specific test mode after a reset. In the simplest case, a measurement routine can be initiated, in which the reusable 126 is supplied with a test current. For example, the test current may be supplied via the sensor coupling 148 and, more particularly, via one or more of the contacts 180. By way of example, the network 192 in FIG. 8 can be used for this purpose. By way of example, the current introduced by the network 192 can be measured and stored. The measured value would deviate from the prescribed value in the case of leakage currents. By way of example, the measurement can be carried out permanently or over relatively long time-intervals. Storage is possible in a data storage medium of the reusable 126. The values thus stored in the reusable 126 can, for example, be used later by the reusable 126 for a test when an actual measurement by a transcutaneous sensor 112 is initiated, and can be converted into an error message when necessary. For example, different measurement values registered during the measurement can be provided with a specific error message. These error messages can be displayed during data interchange between the reusable 126 and a data manager (not illustrated in the figures) and can output, for example, an alert or the like because the reusable 126 generally does not have an option itself for indicating system states visually or otherwise, for example, acoustically.

In a more complex embodiment, which could likewise be implemented with the embodiment of FIG. 8, the protective container 158 could also have its own intelligence in the form of a data-processing device 186. The latter can, for example, have a microcontroller (μC), one or more data storage media, peripheral instruments, firmware or combinations of the aforementioned and/or other elements. Continuing metrological tests can be performed thereby. Information can be interchanged unidirectionally or bidirectionally between the intelligence of the protective container 158 and the reusable 126 via the control connector 168 and the control coupling 146. This interface between the control connector 168 and control coupling 146 can, for example, comprise an SPI, an I2C or a 1-wire bus. This can facilitate the use of not only error statistics with regard to the reusable measurement, but also further diagnostic information, for example, subsequently in the data manager when the contents of the data storage medium of the reusable 126 are wholly or partly transmitted to this data manager. The system can also be extended such that information is transmitted from the data manager to the reusable 126 located in the protective container 158, and from the reusable to the protective container 158. Thus, for example, information can be transmitted to the protective container 158 via the coupling assembly 142, and so the protective container 158 can, if necessary, be conditioned by the user and, for example, be provided with an update, for example a software update. This option can be carried out as an alternative to the use of the above-described optional data interface 184 of the protective container 158, or in addition thereto.

It is also possible to equip the protective container 158 itself with its own user interface. The latter can be used to perform different types of settings via operating elements. Thus, for example, provision can be made for a display, which can include a simple LED indicator, a segmented and/or alphanumeric display, a matrix display or other types of indicator elements or combinations of the aforementioned and/or other indicator elements.

As illustrated above, the reusable 126 can act as a bidirectional communication channel from and/or to the data manager when inserted into the protective container 158. The display and entry functions of the data manager can thus also be used as an operating console for the protective container 158. Alternatively, or in addition thereto, the protective container 158 can also communicate directly with the data manager. By way of example, this can take place via the data interface 184. This communication can comprise radio communication. The user interface and/or the display of the data manager can also be used to influence the functionality and/or configuration of the protective container 158.

As the protective container 158 requires more energy, particularly in the latter cases, the protective container 158 is advantageously equipped with a sufficiently large energy supply 188, for example at least one primary battery and/or a secondary battery or it is even, as an alternative or in addition thereto, provided with a mains connection. The latter can be used for direct current supply, but can also act as a charger for the at least one electrical energy storage device. As a result, the protective container 158 can be used both on the move and in stationary situations.

Further possible embodiments relate to the above-described function test. Thus, a test procedure can consist of a single leakage-current measurement. Alternatively, or in addition thereto, the test procedure can also comprise registering a continuum of values over a defined period of time in order to derive a further-reaching diagnosis and/or, where necessary, differentiated information or messages from this time-based information. By way of example, this allows the detection of changes in resistance over time (for example as a result of aging or contamination effects), artifacts or similar effects.

Furthermore, the protective container 158 can be provided with real-time information. By way of example, this can be synchronized by the data manager in a similar fashion to the reusable 126. Alternatively, or in addition thereto, provision can also be made for an independent real time clock (RTC) in the protective container 158. In general, this allows the assignment of real times to measured values and, if necessary, error messages, for example, by appending in a data storage medium.

In a matched fail-safe embodiment, the protective-container-side functions can also be controlled on the level of the reusable 126, and so only a passive network is required at the connector 164. In this case, tests are generally only possible if the reusable 126 is completely functional.

When the box, i.e., protective container 158, has its own intelligence and an independent communication channel, leakage-current determinations can be determined and reported independently of the reusable electronics. Such a redundant system further increases the safety of the system. In addition to leakage-current measurements, it is also possible to simulate and/or test, for example, voltages at the reference electrode and/or the counter electrode.

The optional communication channel to the protective container 158, for example, the data interface 184, can be wireless or wired and can have a unidirectional or advantageously a bidirectional design. This data interface 184 can be implemented in a wired or a wireless fashion, the latter being based on, for example, optical systems or radio. An internet connection is also possible.

If the passive network of the protective container 158 is replaced and/or extended by one or more active current sources and/or voltage sources, this also allows readjusting of the reusable 126. This readjustment can be carried out as an alternative to a calibration, or in addition thereto, with the term "calibration" conventionally relating to another type of measurement of the analyte concentration in conjunction with referencing, for example, referencing to whole blood by means of one or more test elements, for example, test strips.

A calibration or re-calibration can, as an alternative or in addition thereto, be carried out by means of the protective container 158. Thus, for example, the transcutaneous sensor system 110 can be calibrated relative to whole blood, which is established separately by a so-called spot measurement instrument. By way of example, this can comprise a test-strip measurement instrument or another type of measurement instrument for detecting the at least one analyte, which can, for example, be integrated into the data manager, or can be designed separately. In respect thereof, reference can be made to US Pub. No. 2008/0242962 A1 which is incorporated herein by reference. Alternatively, or in addition thereto, such a measurement instrument can also be integrated into the protective container 158. By way of example, a measurement instrument with a replaceable reference-sensor element can be integrated in the protective container 158, which measurement instrument can, for example, be wetted by a defined glucose reference solution or analyte reference solution. The reference-sensor element can then be connected to the reusable 126 via the connector assembly 164 and the coupling assembly 142 and the measured value can be associated with the defined glucose value (or generally an analyte concentration) in the reusable 126. A complete measurement system integrated into the protective container 158 would also be feasible, for example, a whole blood measurement system. Using this, a replaceable sensor of the integrated measurement system could, for example, be wetted with whole blood or another type of bodily fluid and could, for example, be connected serially to an internal measurement system of the protective container 158, and via the latter system in turn to the reusable 126 via the connector assembly 164 and the coupling assembly 142. By way of example, a quotient formed from both measurements could subsequently serve as a basis for calibrating the transcutaneous sensor system 110.

Since a multiplicity of different components occur in the above description and a multiplicity of different terms are used for groups of these components, these terms are summarized below.

As used herein a transcutaneous sensor system 110 is generally understood to be a group of system components, whether or not they are connected to one another by mechanical and/or electrical means, which include at least one transcutaneous sensor 112 and at least one reusable control part 118 and also, optionally, at least one control component 120 and at least one attachment element 122.

The reusable 126, which is also referred to as a reusable control part 118 (the two terms are largely used synonymously), is understood to be a component that comprises at least one electronics component for actuating and/or evaluating the transcutaneous sensor 112. By way of example, this component can comprise electronics for measuring the sensor current, for controlling the transcutaneous sensor 112 and/or for communicating with peripherals, for example, with a data manager. The data manager, which is not illustrated in the figures, can likewise be part of the transcutaneous sensor system 110. By way of example, the reusable 126 may be designed to be re-used about 50 times.

In general terms, the term "transcutaneous" sensor system indicates the use of a transcutaneous sensor 112, that is to say a sensor which is designed for measuring from within a body tissue. Hence, the term "transcutaneous" can describe both completely implanted sensors, which do not have a wired or other material connection through the skin of the user, and also sensors in which at least one such connection is led through the skin of the user.

As used herein, the disposable 124 should generally be understood to be a group of connected or separately designed parts, which should only be used for one measurement cycle. By way of example, this group can comprise the transcutaneous sensor 112, an insertion needle and/or an insertion instrument, the control component 120 and/or combinations of the aforementioned and/or other disposable elements.

In general, the bodymount 128 can be understood to be that functional group that includes the control component 120 and, where necessary, the attachment element 122. The functional unit made of transcutaneous sensor 112, bodymount 128 and reusable 126 can also be referred to as a patch.

Furthermore, the group comprising the protective container 158 and at least one reusable 126 is referred to as a "kit" 156 herein. The group that comprises the kit 156 and at least one transcutaneous sensor 112 and optionally at least one control component 120 and also, alternatively or in addition thereto, at least one data manager is referred to as a sensor device 157 herein. A sensor device 157 can thus comprise the transcutaneous sensor system 110 and, additionally, the at least one protective container 158.

Figure 9:
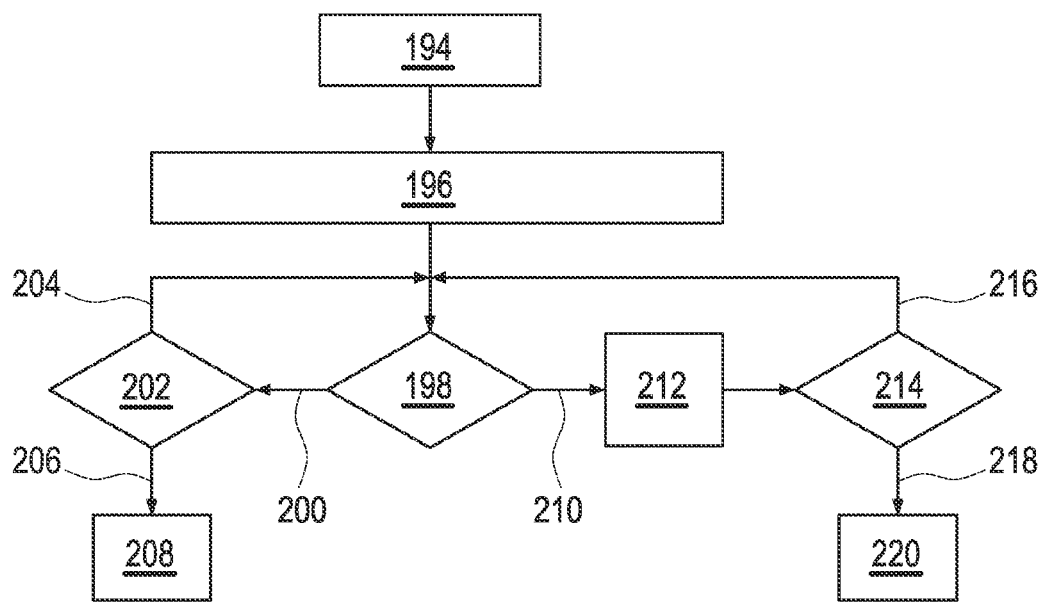
FIG. 9 is a flow chart of a fail-safe routine.

FIG. 9 illustrates a method for functional testing of the reusable 126, which can, for example, be carried out with the embodiment illustrated in FIG. 8 and other suitable embodiments of the protective container 158. In a step 194, the reusable 126 is first of all introduced into the protective container 158, for example, by insertion or by "plugging in." When inserting the reusable 126 into protective container 158, the plug connection 144 can, for example, be established. Subsequently, in step 196, the function test is initiated. This initiation can be started automatically, for example by the introduction itself, or manually, for example by a user, or by an external start signal. By way of example, the reusable 126 can be placed into a box mode in the process.

The actual function test is subsequently performed. By way of example, this can, as described above, comprise a leakage-current measurement and/or a resistance measurement. By way of example, a decision can be made in step 198 as to whether the results of the function test meet a predetermined standard, for example whether the results are within one or more intended ranges or, for example, exceed one or more thresholds. By way of example, one or more resistances and/or one or more leakage currents can be compared to one or more thresholds.

If the result is satisfactory (branch 200), it is possible, for example, to query whether removal should take place. Should this not be the case (branch 204), it is possible to repeat the function test in step 198. If the reusable 126 is removed from the protective container 158 (branch 206) it can be utilized in the performance of a regular measurement 208 in a transcutaneous sensor system 110.

By contrast, if the result is found to be unsatisfactory in step 198, and thus does not meet the standard (branch 210), an error status can be stored in the reusable 126 in method step 212. For example, box 212 can correspond to the storage of an error status in a non-volatile data storage medium such as an EEPROM or flash EPROM of the reusable 126. There can subsequently be another query 214 as to whether removal should take place or not. The function test can be repeated if this is not the case (branch 216). By contrast, if the reusable 126 is removed (branch 218), the error message relating to the error status stored in step 212 can be transmitted to the data manager as indicated by box 220. After transmission tot eh data manager, this error status can, for example, be used to prevent a measurement, to characterize the measurement values as unreliable, to warn a user or to initiate other types of error routines.

Figure 10:
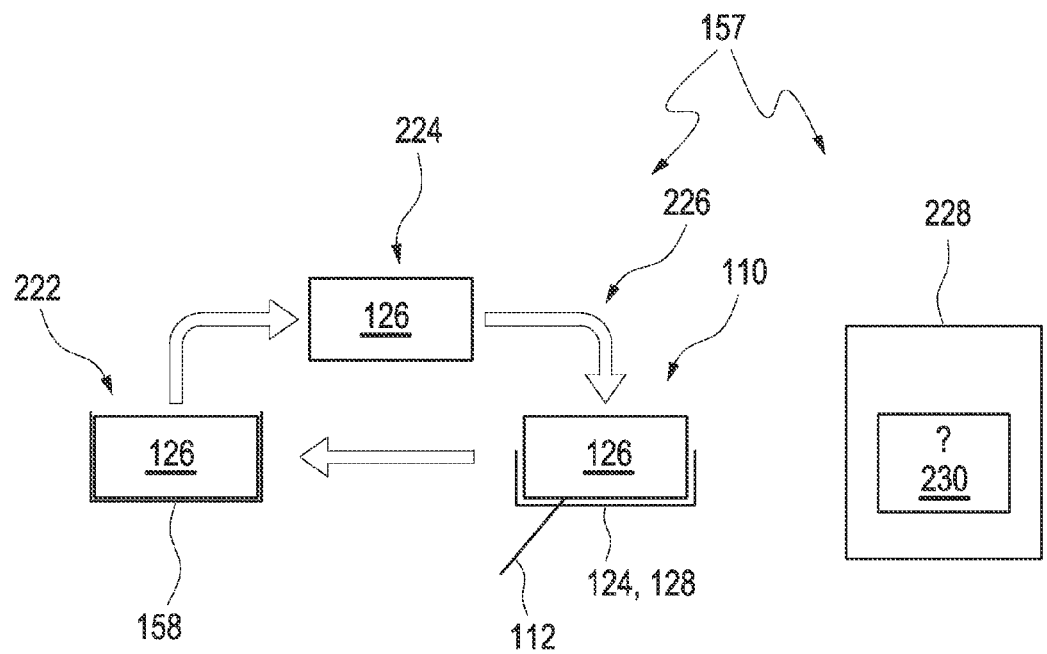
FIG. 10 schematically depicts a first exemplary embodiment of a method for protecting a reusable control part of a transcutaneous sensor system.
Figure 11:
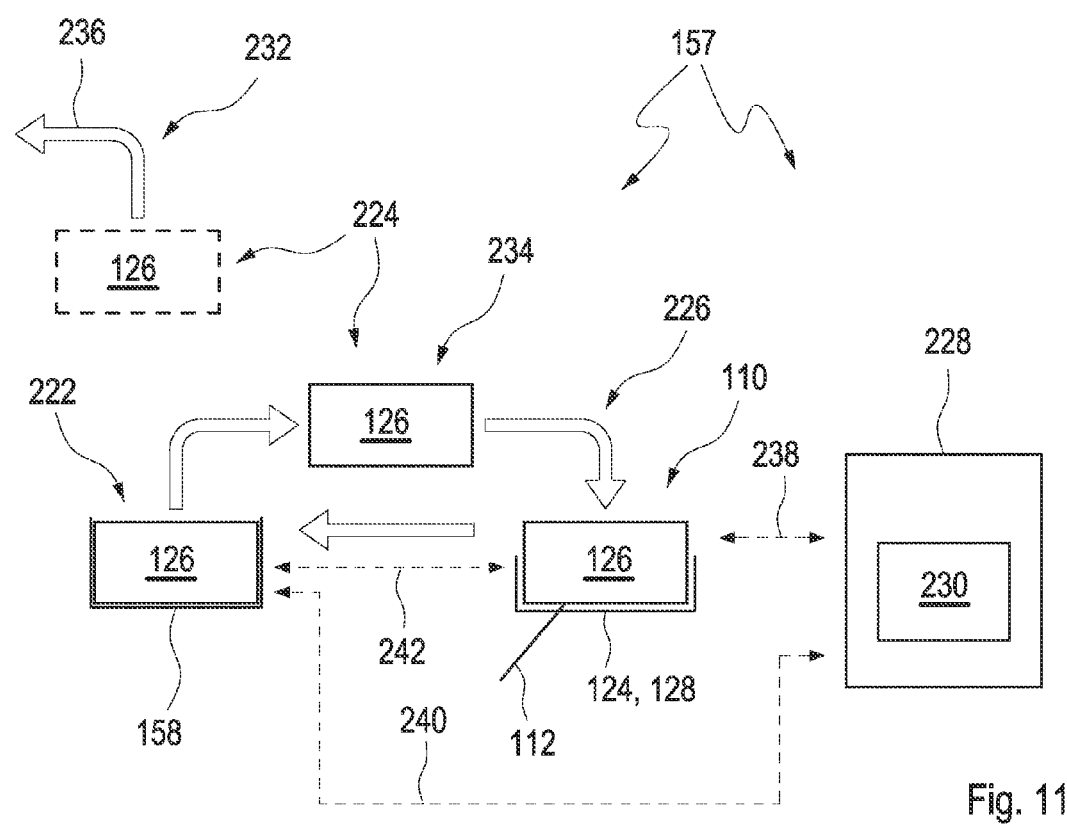
FIG. 11 schematically depicts a second exemplary embodiment of a method for protecting a reusable control part of a transcutaneous sensor system.

FIGS. 10 and 11 show two exemplary embodiments of methods for protecting the reusable 126 and for operating the sensor device 157. In FIGS. 10 and 11, the reusable 126 is illustrated at different points in a cycle, with the reusable 126 at one point being held in the protective container 158 (position 222), at one point in the free unconnected state (position 224) and at one point held in the transcutaneous sensor system 110 (position 226), for example, together with the sensor 112 and the bodymount 128. The arrows indicate that change between the positions 222, 224 and 226 can occur repeatedly.

A data manager 228 is also illustrated in FIGS. 10 and 11. By way of example, this data manager 228 can wirelessly retrieve data from the reusable control part 118, for example, when the latter is integrated into the transcutaneous sensor system 110. By way of example, the above-described telemetry component 140 can be used for this purpose. The data manager 228 can, for example, comprise an indicator element 230, which can be used to display, for example, measurement information and/or the status of the reusable 126, for example, the result of the function test. Furthermore, the data manger 228 can have database functions, functions for displaying past measurement values, storage functions, administration functions or other functions known to be used with a data manager of a medical system. Furthermore, the data manager 228, which can be a component of the transcutaneous sensor system 110, can also, as described above, comprise at least one measurement instrument for detecting the at least one analyte in the bodily fluid. For example, the measurement instrument may be a spot measurement instrument by means of which the at least one analyte is detected qualitatively or quantitatively by means of at least one test element, for example, a test strip.

FIG. 10 shows an exemplary embodiment in which the protective container 158 merely has passive protective functions such as protective functions against moisture and contaminants and, optionally, ESD protection. By way of example, the protective container 158 can be the exemplary embodiment of FIG. 6. If the reusable 126 is removed from the protective container 158 (position 224), the status of this reusable 126 will typically be unknown. Neither the protective container 158, if solely passive, nor, typically, the reusable 126 itself stores information relating to the functionality status of reusable 126 because this function information is not available. For example, such information could relate to leakage currents and/or resistances. Although the passive protective functions of the protective container 158 reduce the probability of the reusable 126 being faulty, should errors nevertheless occur these are, in the worst case scenario, only identifiable when the reusable 126 is integrated into the transcutaneous sensor system 110, as illustrated in position 226. In this scenario, the data manager 228 has no information with regard to the error status of the reusable 126 at its disposal, as indicated by the question mark in FIG. 10.

By contrast, in the exemplary embodiment depicted in FIG. 11, the protective container 158 has one or more active functions. By way of example, the protective container can include all or some of the functions shown in FIG. 8. By way of example, the protective container 158 itself can be set up to perform a function test. The protective container 158 can alternatively or additionally include indicator functions to output an error message if the function test indicates deviations from an intended range by certain functions, such as resistances and/or leakage currents. By way of example, this allows the output of the message "error" or "pass" (no error). This output, however, is optional. Furthermore, other outputs are also possible.

If the reusable 126 is removed from the protective container 158 (positions 224 in FIG. 11), it is possible for the reusable 126 to be defective (position 232) or for the reusable to operate as planned (position 234). By way of example, this information relating to the state of the reusable 126 can, as explained above, be stored in a non-volatile data storage medium or another type of data storage medium of the reusable 126. If the faultiness of the reusable (position 232) has previously been displayed by the protective container 158 itself, for example, by an indicator element of the protective container 158 and/or of an instrument connected to the protective container 158, the reusable 126 can be directly disposed of from position 232 (arrow 236) and/or returned to the manufacturer or a service company.

By contrast, if it was indicated that the reusable 126 is free from errors (position 234), the reusable 126 can be inserted into the transcutaneous sensor system 110. The data manager 228 can initiate a status query 238 of the status stored in the reusable 126 so the reusable status can, for example, be indicated on the indicator element 230. Alternatively, or in addition thereto, there can also be direct information transfer 240 between the data manager 228 and the protective container 158. This information transfer, which can take place in a unidirectional or bidirectional fashion, can, for example, take place when the reusable 126 is still inserted in the protective container 158 (position 222), or, alternatively or in addition thereto, at a later time when the protective container 158 is empty. By way of example, this allows direct communication between the data manager and protective container 158. With such direct communication, the data manager 228 can, for example, also indicate and/or influence functions of the protective container 158.

There can also be direct information transfers 242 between the transcutaneous sensor system 110 and the protective container 158 in this and in other exemplary embodiments. This allows the protective container 158 itself to take over, wholly or partly, the functions of the data manager 228. For example one, a number of, or all of the above-described functions of the data manager 228 could be performed by alternative embodiments of the protective container 158. Hence, the data manager 228 can optionally be wholly or partly integrated into the protective container 158 in the illustrated exemplary embodiments and in other embodiments of the present invention.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

110 Transcutaneous sensor system
112 Transcutaneous sensor
114 Sensor plug
116 Sensor region
118 Control part
120 Control component
122 Attachment element
124 Disposable
126 Reusable
128 Bodymount
130 Electrical energy storage device
132 Data storage medium
134 Control plug
136 Microcontroller
138 Actuation and evaluation electronics
140 Telemetry component
142 Coupling assembly
144 Plug connection
146 Control coupling
148 Sensor coupling
150 Hole
152 Base plate
154 Sealing element
156 Kit
157 Sensor device
158 Protective container
160 Container housing
162 Inner space
164 Connector assembly
166 Sensor connector
168 Control connector
170 Sealing element
172 Closure element
174 Sealing element
176 Desiccant
178 ESD protection
179 Ground line
180 Contacts
182 Interface
184 Data interface 186 Data-processing device
188 Energy supply
190 Data storage medium
192 Network
194 Inserting reusable into protective container
196 Initiate function test
198 Result satisfactory?
200 Result satisfactory
202 Removal?
204 No removal
206 Removal
208 Regular measurement
210 Result satisfactory
212 Storing error status in reusable
214 Removal?
216 No removal
218 Removal
220 Transmitting error status to data manager
222 Reusable in protective container
224 Reusable free
226 Reusable in the transcutaneous sensor system
228 Data manager
230 Indicator element
232 Reusable defect
234 Reusable OK
236 Disposal
238 Status query
240 Information transfer
242 Information transfer

What is claimed is:

1. A protective container for holding a reusable control part of a transcutaneous sensor system for detecting at least one analyte in a bodily fluid, wherein the control part includes at least one coupling assembly having a sensor coupling for connection to at least one transcutaneous sensor when the control part is being used, wherein the protective container comprises: at least one container housing, wherein the control part is positionable in the container housing when the control part is not in use, wherein the container housing is adapted to shield the control part from environmental influences, and wherein the container housing has a connector assembly with at least one sensor connector, the at least one sensor connector being connectable to the sensor coupling and forming a sealing engagement with the sensor coupling when connected thereto and wherein the protective container has at least one electrical energy supply, the coupling assembly of the control part being engageable with only one of the transcutaneous sensor and the sensor connector of the protective container at any one time and wherein connecting the connector assembly to the at least one coupling assembly establishes an electrical connection between the connector assembly and the at least one coupling assembly; and a microcontroller disposed within the container housing and powered by the at least one electrical energy supply, the microcontroller being in communication with an interface and with the control part when the connector assembly is connected to the at least one coupling assembly thereby adapting the protective container to communicate calibration information from an external measuring instrument to the control part when the connector assembly is connected to the at least one coupling assembly.

2. The protective container of claim 1 wherein the at least one electrical energy supply comprises an internal energy supply.

3. The protective container of claim 2 wherein the internal energy supply comprises a battery.

4. The protective container of claim 3 wherein the battery is a rechargeable battery.

5. The protective container of claim 1 wherein the at least one electrical energy supply comprises a coupling for an external energy supply.

6. The protective container of claim 5 wherein the coupling for an external energy supply comprises a mains plug.

7. The protective container of claim 1 further comprising a user interface powered by the at least one electrical energy supply.

8. The protective container of claim 1 wherein the container housing comprises an electrically conductive material and thereby at least partially electrically shields the control part when the control part is received in the container housing.

9. The protective container of claim 1 wherein the protective container is adapted to supply electrical power from the at least one electrical energy supply when the connector assembly is connected with the at least one coupling assembly.

* * * * *